United States Patent
Mary et al.

(10) Patent No.: US 6,579,858 B1
(45) Date of Patent: *Jun. 17, 2003

(54) USE OF LOW-MOLECULAR-WEIGHT HEPARINS FOR THE PREVENTION AND TREATMENT OF CEREBRAL EDEMAS

(75) Inventors: Véronique Mary, Evry (FR); Jérémy Pratt, Paris (FR); Jean-Marie Stutzman, Villecresnes (FR); André Uzan, Paris (FR); Florence Wahl, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/450,110

(22) Filed: Nov. 29, 1999

Related U.S. Application Data

(63) Continuation of application No. PCT/FR98/01035, filed on May 25, 1998.

(30) Foreign Application Priority Data

May 28, 1997 (FR) ............................................ 97 06551

(51) Int. Cl.$^7$ ..................... A61K 31/727; C08B 37/10
(52) U.S. Cl. ............................................. 514/56; 536/21
(58) Field of Search ............................... 514/56; 536/21

(56) References Cited

FOREIGN PATENT DOCUMENTS

RU         2013092        5/1994

OTHER PUBLICATIONS

Pratt et al. Haemostasis Mar.–Apr. 1998, 28(2), 78–85.*
Physician's Desk Reference, 1995, 49th Edition, Medical Economics Data Production Company, Montvale, New Jersey, pp. 1968–1969.*

Bes, et al., "Medical Therapeutic Strategy of Acute Cerebral Ischaemia in Adults,"J. Neuroradiol, 20, 102–120 (1993).

Van Gijn, "Thrombolysis in Ischemic Stroke: Double or Quits?." Circulation, 93, 1616–17 (1996).

Marx, "Die Therapie des Akuten Ischamischen Insultes," Hamostaseologie, 17, 86–91 (1997). In German.

Fareed et al., "Comparative Study on the in vitro and in vivo Activities of Seven Low–Molecular–Weight Heparius," Haemostasis, 18 (suppl. 3), 3–15 (1988).

Fujii et al., "Treatment for Delayed Brain Injury After Pituitary Irradiation," Neurol. Surg., 16(3), 241–247 (1988). (English–language Abstract Only).

Green et al., "Prevention of Thromboembolism after Spinal Cord Injury Using Low–Molecular–Weight Heparin," Annal. Intern. Med., 113, 571–574 (1990).

Kay et al., "Low–Molecular–Weight Heparin for the Treatment of Acute Ischemic Stroke," New Eng. J. Med., 333(24), 1588–1593 (1995).

DiStefano et al., "Low–Molecular–Weight Heparins for Long–Term Therapy of Peripheral Vascular Disease," Therapeut, Res., 44(1), 1–9 (1988).

Tzonos et al., "The Effect of Proteinasen and Fibrinolysis Inhibitors on Experimental Brain Edemo," Z. Neurol., 205(1), 61–70 (1973). (English language abstract only).

* cited by examiner

Primary Examiner—Kathleen K. Fonda
(74) Attorney, Agent, or Firm—Irving Newman

(57) ABSTRACT

Cerebral edema is prevented and treated by administering an effective amount of a low molecular weight heparin.

9 Claims, No Drawings

USE OF LOW-MOLECULAR-WEIGHT HEPARINS FOR THE PREVENTION AND TREATMENT OF CEREBRAL EDEMAS

CROSS-REFERENCE TO RELATED APPLICATIONS

This application is a continuation of international Application No. PCT/FR98/01035, filed May 25, 1998.

The present invention relates to the use of low-molecular-weight heparins for the prevention and treatment of cerebral edemas.

The invention also relates to the use of low-molecular-weight heparins for the preparation of a medicament for the prevention and treatment of cerebral edemas.

Standard heparin is a sulphated polysaccharide having an average molecular weight of 12,000–15,000 daltons which is isolated from bovine, ovine and porcine intestinal mucous membranes. Heparin is clinically used for the prevention and treatment of thromboembolic disorders but sometimes causes haemorrhages.

Over the past ten years, heparin has been gradually replaced by low-molecular-weight heparins which no longer exhibit or which exhibit to a lesser degree the disadvantage of causing bleeding and which now require only one injection per day instead of 2 to 3 injections per day for standard heparin. These low-molecular-weight heparins are prepared in particular by fractionation, controlled depolymerization of heparin or by chemical synthesis. They have an anti-Xa activity/anti-IIa activity ratio greater than 2.

It has now been found that low-molecular-weight heparins reduce cerebral edemas.

Cerebral edemas represent a major aggravating consequence of thromboembolic cerebrovascular accidents, of cerebral haemorrhages and of traumas of the central nervous system (cerebral trauma or medullary trauma) but also of cardiac and/or respiratory arrests, or any functionally equivalent situation regardless of its origin (ventricular fibrillation, malignant asthma attack). Cerebral edemas can also be found in any pathological or accidental situation of coma accompanied by hypoperfusion of the cerebral parenchyma. Cerebral edemas may also accompany cerebral tumours, irradiations and bacterial, viral and parasitic infections of the cerebral parenchyma.

According to the invention, a low-molecular-weight heparin having an average molecular weight of between 1000 and 10,000 daltons, in particular between 1500 and 6000 daltons, and in particular between 4000 and 5000 daltons is preferably used.

They can be prepared by various processes from heparin:
fractionation by means of solvents (FR 2,440,376, U.S. Pat. No. 4,692,435),
fractionation on an anionic resin (FR 2,453,875),
gel filtration (BARROWCLIFFE, Thromb. Res. 12, 27–36 (1977)),
affinity chromatography (U.S. Pat. No. 4,401,758),
controlled depolymerization by means of a chemical agent: nitrous acid (EP 14184, EP 37319, EP 76279, EP 623629, FR 2,503,714, U.S. Pat. No. 4,804,652; WO 813276), β-elimination from a heparin ester (EP 40144, U.S. Pat. No. 5,389,618), periodate (EP 287477), sodium borohydride (EP 347588, EP 380943), ascorbic acid (U.S. Pat. No. 4,533,549); hydrogen peroxide (U.S. Pat. No. 4,629,699, U.S. Pat. No. 4,791,195), quaternary ammonium hydroxide from a quaternary ammonium salt of heparin (U.S. Pat. No. 4,981,955), alkali metal hydroxide (EP 380943, EP 347588) or by an enzymatic route (EP 64452, U.S. Pat. No. 4,396,762, EP 244235, EP 244236; U.S. Pat. No. 4,826,827; U.S. Pat. No. 3,766,167); by means of irradiation (EP 269981).

Some can also be prepared by chemical synthesis (U.S. Pat. No. 4,801,583, U.S. Pat. No. 4,818,816, EP 165134, EP 84999, FR 2,535,306).

Among these low-molecular-weight heparins, there may be mentioned more particularly enoxaparin (INN) marketed by RHONE-POULENC RORER, nadroparin (INN) marketed by SANOFI, parnaparin (INN) marketed by OPOCRIN-ALFA, reviparin (INN) marketed by KNOLL, dalteparin (INN) marketed by KABI PHARMACIA, tinzaparin (INN) marketed by NOVO NORDISK, danaparoid (INN) marketed by ORGANON, ardeparin (INN) developed by WYETH AYERST, certoparin (INN) marketed by SANDOZ and products under study such as CY222 from SANOFI-CHOAY (Thromb. Haemostasis, 58 (1), 553 (1987)), SR90107/ORG31540 from SANOFI-ORGANON (Thrombosis and Haemostasis, 74, 1468–1473 (1995)).

Preferably, the low-molecular-weight heparins consist of oligosaccharides having a 2-O-sulpho-4-enopyranosuronic acid at one of their ends.

A particularly advantageous low-molecular-weight heparin is obtained by depolymerization of a heparin ester by means of a base such as sodium hydroxide.

A The preventive action of low-molecular-weight heparins on edema was determined in rats after photothrombotic cerebral lesion according to the following protocol: male Sprague-Dawley rats (150–200 g) (26 for the treated group and 22 for the control group) are anaesthetized with chloral hydrate (400 mg/kg ip) and placed under stereotaxic frame. The skin is incised to reveal the skull and a cold light (Bioblock 150W) is brought into contact with the right-hand side of the skull in front of the lambda. The low-molecular-weight heparins are dissolved in a saline solution (0.9% NaCl) and the procedure is continued as follows:

3 hours before the lesion, 2 mg/kg/5 ml of low-molecular-weight heparin are injected by subcutaneous route, just before the lesion, 0.5 mg/kg/5 ml of low-molecular-weight heparin is injected by the intravenous route, and immediately after, 10 mg/kg/5 ml of rose bengal dye in a saline solution (0.9% NaCl) are injected by the subcutaneous route, the lesion is then made by illuminating the skull for 5 minutes and then the skin is sutured and the animals are returned to their cages, 3 hours and 21 hours after the lesion, 2 mg/kg/5 ml of low-molecular-weight heparin are injected by the subcutaneous route, 24 hours after the lesion, the animals are decapitated and the brains are recovered.

Samples are collected at the site of the lesion and contralaterally to the lesion using a cork borer 6 mm in diameter. The volume of water in the samples is determined by the tissue wet weight/tissue dry weight ratio and the edema expressed as the percentage of excess water on the lesioned sample compared with the sample from the contralateral hemisphere for each rat. The control animals receive physiological saline under the same conditions.

In this test, the low-molecular-weight heparins reduce the edema by about 30%.

Enoxaparin reduces the edema by 33%.

These results demonstrate that low-molecular-weight heparins have a preventive effect on edema.

B The curative action of low-molecular-weight heparins on edema was determined in rats after photothrombotic cerebral lesion according to the following protocol: male Sprague-Dawley rats (200–240 g) (20 for the control group and 12 and 8 for the treated groups) are anaesthetized with chloral hydrate (400 mg/kg ip) and placed in a stereotaxic frame. The skin is incised to reveal the skull and a cold light (Bioblock 150W) is brought into contact with the right-hand side of the skull in front of the lambda. 10 mg/kg/5 ml of rose bengal dye in physiological saline are injected by the intravenous route. The skull is then illuminated for 5 minutes. The skin is then sutured. The low-molecular-weight heparins are dissolved in a saline solution (0.9% NaCl) and then, either 2 hours after the lesion, 0.5 mg/kg/5 ml of low-molecular-weight heparin is injected by the intravenous route and then 15 minutes after the lesion, 2 mg/kg/5 ml of low-molecular-weight heparin are injected by the subcutaneous route, or 6 hours after the lesion, 2 mg/kg/5 ml of low-molecular-weight heparin are injected by the subcutaneous route. The animals are returned to their cages. 24 hours after the lesion, the animals are decapitated and the brains are collected. Samples are collected at the site of the lesion and contralaterally to the lesion using a cork borer 6 mm in diameter. The volume of water is determined by the tissue wet weight/tissue dry weight ratio and the edema expressed by the percentage of excess water on the lesioned sample compared with the sample from the contralateral hemisphere for each rat. The control animals receive physiological saline under the same conditions.

In this test, the low-molecular-weight heparins reduce the edema by about 30% when the low-molecular-weight heparin is injected 2 hours or 6 hours after the lesion.

Enoxaparin reduces the edema by 33% in the 2 cases.

In the same test, but in which the low-molecular-weight heparins are injected 18 hours after the lesion (0.5 mg/kg/5 ml by the intravenous route and then 15 minutes later 2 mg/kg/5 ml by the subcutaneous route), the reduction in the edema is still significant since it is about 10 to 30% (enoxaparin 23% and nadroparin 14%).

These results demonstrate that low-molecular-weight heparins have a curative effect on edema.

C The effect of low-molecular-weight heparins on cerebral edema is also demonstrated in rats on edema induced by a trauma according to the following technique: male Sprague-Dawley rats (Charles River France) weighing 280–300 g (12 for the control group and 12 for the treated group) are anaesthetized with halothane (1.5%) in an $N_2O/O_2$ (70/30) mixture and placed in a stereotaxic frame. The epicranium is incised and a hole is made by means of a toothed drill at the level of the right parietal cortex (coordinates: 3.5 mm before, 6 mm above the interaural line). A polyethylene tube with an internal diameter of 3 mm is placed on the dura mater, fixed in the cranial cavity with dental cement and connected to a solenoid valve (Danfoss Evsi 24 v, 15W).

The dura mater is kept intact. The valve is connected to a HPLC pump (Walters 590). The system is filled with sterile water and when the pump has reached a pressure of 3.8 to 4 bar, the fluid impact of moderate severity (1.6–1.8 bar) is induced by a brief opening (20 ms) of the valve. The tube is then withdrawn, the incision sutured and the animals are returned to their cage in a room heated to 26–28EC.

The low-molecular-weight heparins dissolved in a saline solution (0.9% NaCl) are administered in the following manner: 2 hours after the lesion: 0.5 mg/kg/5 ml IV bolus, 2 hours 15 minutes after the lesion: 2 mg/kg/5 ml SC, 6 hours after the lesion: 2 mg/kg/5 ml SC, 24 hours after the lesion: 2 mg/kg/5 ml SC and 30 hours after the lesion: 5 mg/kg/5 ml SC.

5 ml/kg of a saline solution (0.9% NaCl) are administered to the control group under the same conditions.

The animals are sacrificed 48 hours after the lesion. The cerebral edema is evaluated according to the wet weight/dry weight technique (24 hours at 100EC). The edema, evaluated as the water content of the brain, is measured in the hippocampus and the cortex adjacent to the lesion site.

In this test, the low-molecular-weight heparins reduce by at least 40% the edema in the hippocampus and in the cortex adjacent to the lesion site.

Enoxaparin (LOVENOX7) reduces the edema by 69% in the hippocampus and by 50% in the cortex adjacent to the lesion site.

The medicaments consist of a salt (preferably sodium or calcium) of a low-molecular-weight heparin in the form of a composition in which it is combined with any other pharmaceutically compatible product which may be inert or physiologically active. The medicaments according to the invention may be used by the intravenous, subcutaneous, oral, rectal, topical or pulmonary (inhalation) route.

Sterile compositions for intravenous or subcutaneous administration are generally aqueous solutions. These compositions may also contain adjuvants, in particular wetting, isotonizing, emulsifying, dispersing and stabilizing agents. The sterilization can be carried out in several ways, for example by aseptisizing filtration, by incorporating sterilizing agents into the composition, by irradiation. They may also be prepared in the form of sterile solid compositions which may be dissolved at the time of use in sterile water or any other injectable sterile medium.

As solid compositions for oral administration, there may be used tablets, pills, powders (gelatine capsules, cachets) or granules. In these compositions, the active ingredient is mixed with one or more inert diluents such as starch, cellulose, sucrose, lactose or silica, under an argon stream. These compositions may also comprise substances other than diluents, for example one or more lubricants such as magnesium stearate or talc, an agent promoting oral absorption, a colorant, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavouring or stabilizing products.

The compositions for rectal administration are suppositories or rectal capsules which contain, in addition to the active ingredient, excipients such as cocoa butter, semisynthetic glycerides or polyethylene glycols.

The compositions for topical administration may be, for example, creams, lotions, collyria, collutoria, nasal drops or aerosols.

The doses depend on the desired effect, the duration of treatment and the route of administration used; they are generally between 0.2 mg and 4 mg per kg per day by the subcutaneous route, that is to say 14 to 280 mg per day for an adult.

In general, the doctor will determine the appropriate dosage according to the age, weight and any other factors specific to the subject to be treated.

The present invention also relates to the method for the prevention or treatment of cerebral edemas in humans comprising the administration of an effective quantity of a low-molecular-weight heparin.

What is claimed is:

1. In a method for treating cerebral edema in a mammal, the method comprising administering to said mammal an effective amount of a pharmaceutical composition comprising a low molecular-weight heparin.

2. In a method for preventing cerebral edema in a mammal that has suffered cerebral hemorrhage, cerebral or medullary trauma of the central nervous system, cardiac arrest, respiratory arrest, ventricular fibrillation, malignant asthma attack, coma accompanied by hypoperfusion of the cerebral parenchyma, cerebral tumor, irradiation or bacterial, viral or parasitic infection, the method comprising administering to said mammal an effective amount of a pharmaceutical composition comprising a low molecular-weight heparin.

3. In a method for preventing cerebral edema in a mammal that has suffered thromboembolic cerebrovascular accident, the method consisting essentially of administering to said mammal an effective amount of a pharmaceutical composition consisting essentially of a low molecular-weight heparin.

4. The method of claim 1, 2 or 3, wherein said low-molecular-weight heparin has an average molecular weight of between 1,000 and 10,000 daltons.

5. The method of claim 1, wherein said low-molecular-weight heparin has an average molecular weight of between 1500 and 6000 daltons.

6. The method of claim 5, wherein said low-molecular-weight heparin has an average molecular weight of between 4000 and 5000 daltons.

7. The method of claim 1, 2 or 3, wherein said low-molecular-weight heparin comprises at least one oligosaccharide having a 2-O-sulpho-4-enopyranosuronic acid at one end.

8. The method of claim 1, 2 or 3, wherein said low-molecular-weight heparin is obtained by depolymerization of a heparin ester by means of a base.

9. The method of claim 1, 2 or 3, wherein said low-molecular-weight heparin is selected from the group consisting of enoxaparin, nadroparin, parnaparin, reviparin, dalteparin, tinzaparin, danaparoid, ardeparin, certoparin, CY222 and SR90107/ORG31540.

* * * * *